United States Patent [19]

Cleeland, Jr. et al.

[11] 3,972,992

[45] Aug. 3, 1976

[54] DIAGNOSTIC TEST FOR OPIUM ALKALOIDS

[75] Inventors: Roy Cleeland, Jr., Short Hills, N.J.; Hans Jacob Hager, New York City, N.Y.

[73] Assignee: Hoffmann-La Roche Inc., Nutley, N.J.

[22] Filed: Feb. 28, 1975

[21] Appl. No.: 553,942

Related U.S. Application Data

[62] Division of Ser. No. 374,849, June 29, 1973, Pat. No. 3,888,864.

[52] U.S. Cl. .......................... 424/12; 260/29.6 HN; 424/8; 424/78; 424/81; 424/260; 526/220; 526/317
[51] Int. Cl.² ............... A61K 31/74; A61K 31/485; G01N 31/00; G01N 33/16
[58] Field of Search .................... 424/8, 12, 78, 81; 260/6, 29.6 HN, 80, 112 RB

[56] References Cited

UNITED STATES PATENTS

| | | | |
|---|---|---|---|
| 3,857,931 | 12/1974 | Hager | 424/12 |
| 3,888,864 | 6/1975 | Cleeland | 424/12 |

*Primary Examiner*—James O. Thomas, Jr.
*Assistant Examiner*—A. P. Fagelson
*Attorney, Agent, or Firm*—Samuel L. Welt; George M. Gould; Raymond R. Wittekind

[57] ABSTRACT

Amino lower alkyl ethers of the phenolic hydroxyl group of opium alkaloids are linked via a peptide linkage to carboxylated latex polymers to form reagents which are useful in a sensitive diagnostic test to detect the presence of opium alkaloids in body fluids.

8 Claims, No Drawings

DIAGNOSTIC TEST FOR OPIUM ALKALOIDS

This is a division, of application Ser. No. 374,849 filed June 29, 1973, now U.S. Pat. No. 3,888,864.

BACKGROUND OF THE INVENTION

The large increase in the use of narcotic agents, including the opium alkaloids, by the general population has brought with it a substantial need to improve analytical techniques for the determination of such agents in biological fluids. In many instances, medical treatment centers are faced with the need for determining the identity of a narcotic agent taken by a patient who, being in a comatose condition, is unable to supply such information to the treating physician. Early procedures involved the identification of opium alkaloids by extraction and thin-layer chromatographic methods. These techniques have the disadvantages of being relatively time-consuming, laborious and lacking great sensitivity. Recently, a rapid and sensitive immunoassay procedure involving the reaction between antibodies and opium alkaloid antigens was described in U.S. Pat. No. 3,709,868. However, this procedure requires sophisticated equipment such as scintillation counters to be used for the assay. It would, therefore, be desirable to develop a rapid and highly sensitive assay for detecting the presence of opium alkaloids in biological fluids which would not require sophisticated equipment and could be easily performed by laboratory technicians having a minimum of training.

BRIEF DESCRIPTION OF THE INVENTION

The present invention relates to a novel class of opium alkaloid derivatives, namely, amino lower alkyl ethers of the phenolic hydroxyl group of opium alkaloids, which ethers may be covalently coupled via a peptide linkage to a carboxylated latex polymer. The opium alkaloid thus linked to the latex polymer by means of said linking group can then be utilized as a reagent in a sensitive diagnostic assay for the presence of opium alkaloids in biological fluids. This assay method is dependent upon the well known binding of antigen to antibodies specific therefor, which is manifested by an insolubilization or agglutination. When either the antigen or the antibody is linked to a suitable polymer such as a latex polymer, as hereinafter described, the detection of the antigen-antibody binding by means of agglutination is significantly enhanced so that such agglutination reaction is easily visualized by the naked eye.

The general technique of utilizing latex particles as carriers for antigens or antibodies for easy visualization of the antigen-antibody reaction has been previously described in the literature, for example, in Netherlands Pat. No. 7,201,308.

The starting materials which are used for the preparation of the latex reagents of the present invention are amino lower alkyl ethers of the phenolic hydroxyl group of opium alkaloids. As used herein, the term "lower alkyl" is meant to include straight and branched-chain saturated hydrocarbon radicals having from 2 to 8 carbon atoms, inclusive, such as ethyl, propyl, n-butyl, i-butyl, and the like. The opium alkaloids useful for binding to latex polymers are those having free phenolic hydroxyl groups. The opium alkaloid of particular preference in the practice of the present invention is morphine since morphine has a free hydroxyl group in the 3-position and is readily available. Thus, particularly preferred reagents are amino lower alkyl ethers of the phenolic hydroxyl group of morphine. However, the present assay, as hereinafter described, will detect opium alkaloids having either free or functionalized phenolic hydroxyl groups (i.e., morphine, and derivatives of morphine such as codeine and heroin).

The amino lower alkyl ethers of opium alkaloids, as described above, are conveniently prepared from the free phenolic opium alkaloid itself. Utilizing morphine as an example, one can introduce the requisite amino lower alkyl moiety by a number of procedures which are well known in the art. Thus, in a first step, one could alkylate the phenolic hydroxyl group with an appropriate reagent containing a protected amino group or a group which may be easily converted into an amino group. For example, morphine may be alkylated with the appropriate N(halo lower alkyl)-phthalimide in the presence of a base to afford the phthalimido lower alkyl ether of morphine. Thus, for example, morphine may be reacted with N-(3-bromopropyl)-phthalimide to afford the corresponding 3-0-(3-phthalimidopropyl)morphine.

This reaction is carried out in the presence of a base, for example, an alkali metal alkoxide such as sodium methoxide, sodium ethoxide, or potassium tert-butoxide. Suitable solvents for this alkylation reaction include aprotic organic solvents such as dimethylformamide, dimethylsulfoxide or hexamethylphosphoramide. A particularly preferred basic catalyst is potassium tert-butoxide and a particularly preferred solvent is hexamethylphosphoramide.

The reaction may be carried out at a temperature of between about 0° and about +50°C, most preferably at about room temperature.

In the next step, the phthaloyl group may be removed to afford the free amino lower alkyl morphine. Removal of this group is by standard techniques involving the reaction of the phthalimido lower alkyl morphine derivative with a lower alkyl amine such as methylamine. This removal may be carried out in a suitable inert organic solvent, preferably an alcohol such as ethanol. The reaction temperature may be in the range from about 0° to about 50°C, most preferably about room temperature.

In another procedure, the amino lower alkyl group may be introduced by alkylation of morphine with a halo nitrile to afford a cyano lower alkyl ether of morphine, followed by reduction of the nitrile group to an amino methyl group.

For example, morphine may be reacted with 4-bromobutyronitrile to afford 3-0-(3-cyanopropyl) morphine. In such a reaction the halo lower alkyl nitrile is reacted with morphine in the presence of a base, preferably an alkali metal alkoxide. Suitable bases include, for example, sodium methoxide, sodium ethoxide, or potassium tert-butoxide. As suitable solvents for this reaction, there may be mentioned lower alkanols such as methanol, ethanol or tert-butanol. It is preferred to utilize an alkali metal alkoxide which is derived from the solvent employed, for example, sodium ethoxide in ethanol, or potassium tert-butoxide in tert-butanol.

This alkylation reaction may be carried out over a temperature range of from about 20° to about 100°C, most preferably, between about 70° and about 90°C.

The nitrile may be converted to an aminomethyl group by reduction with a complex metal hydride reducing agent. Suitable complex metal hydride reducing agents for this purpose include alkali metal aluminum hydrides such as lithium aluminum hydride. As solvents for this reduction reaction, there may be mentioned ethers such as diethyl ether or tetrahydrofuran. The reduction may be carried out at a temperature of from about 0° to about 100°C, most preferably at about 40° to 60°C.

Other procedures for introduction of the amino lower alkyl moiety onto the phenolic hydroxyl group of an opium alkaloid such as morphine will become readily apparent to one skilled in the art.

In order to prepare the diagnostic reagent useful for the practice of the present invention, the amino lower alkyl ether of the phenolic hydroxyl group of the opium alkaloid is covalently bonded by means of a peptide linkage to a latex polymer containing carboxyl groups.

Suitable latex polymers for this purpose are carboxylated styrene butadienes, carboxylated polystyrenes, acrylic acid polymers, and the like. Among the commercial latex polymers which are included in the aforementioned classes are Amsco Res 4150, Dow 815, Dow 816, Dow 620, Hycar 2600 X 120, Lytron 624 and Rhoplex LC40 3216.

Particularly preferred polymers are carboxylated styrene butadiene co-polymers, preferably Dow 816. Suitable latex carrier particles are generally supplied commercially as an aqueous latex suspension, usually in concentrations of about 40 to about 60% solids. These polymers are water insoluble, have a particle size in the range from about 0.01 to about 0.9 microns, preferably between about 0.1 and 0.3 microns, and a specific gravity near that of water enabling them to remain in aqueous suspension. The particles should have sufficient surface charge density so that when coupled to the amino lower alkyl derivative of an opium alkaloid their repulsive forces are enough to prevent aggregation.

The amino lower alkyl derivatives of the phenolic hydroxy group of an opium alkaloid are coupled to the carboxylated latex polymers by means of an amide linkage initiated in the presence of a water soluble carbodiimide condensing agent. The degree of coupling is dependent upon the density of the reactive groups in the polymer. The density of the reactive groups is not critical to the operability of this invention, as long as a sufficient number of reactive groups are present to provide coupling of a sufficient amount of alkaloid moiety to be useful in a diagnostic test. However, a suitable density would be in the range of from about 1 to about 5%, preferably about 3% by weight. The resulting reagent should contain from about 0.01 to about 15.0% by weight of the alkaloid moiety. The coupling reaction with carbodiimides is described in detail in Netherlands Pat. No. 7,201,308.

Once the latex coupled product is formed, it can be utilized in specific diagnostic tests for the detection of opium alkaloids. It can be used in any convenient concentration, depending upon the specific test and samples involved. However, concentrations of from about 0.1 to about 2% by weight of latex solids are suitable and the preferred concentrations are from about 0.3 to about 1.5% by weight.

In a typical test, a measured amount of antiserum against opium alkaloids is mixed with an opium alkaloid free body fluid, for example, serum or urine, and is incubated at a slightly elevated temperature, e.g., 37°C. Then, a measured amount of amino lower alkyl morphine coupled latex is added and the mixture is allowed to further incubate at the slightly elevated temperature for a period of time, for example, from about 1 to about 3 hrs., preferably for about 2 hrs. The pH of the test mixture is suitably in the range of from about pH 5.0 to 8.0, most preferably about 6.5 to 7.0. After the incubation, flocculation or agglutination of the latex particles is noted. The concentration and quantity of both the antiserum and the latex complex are adjusted to produce a strong flocculation, and the minimum concentrations of both reagents which produce a strong flocculation are determined.

The antisera which may be used in the present diagnostic test are antisera specific for opium alkaloids such as morphine. The preparation of such antisera is described in U.S. Pat. No. 3,709,868.

After the control system is set up, as described above, various amounts of opium alkaloid, e.g., morphine, or a salt thereof, e.g., morphine sulfate, are dissolved in opium alkaloid free body fluid. The minimum amount of opium alkaloid required to inhibit the flocculation is noted. This quantity will depend both upon the concentration and the amount of body fluid added, as well as upon the concentration and the strength of the antiserum utilized in the test.

In a preferred test, the quantities and concentrations are adjusted so that approximately 200 microliters of serum or urine containing between about 100 and 200 nanograms of morphine per milliliter (total of between 20 and 40 nanograms of morphine) will be just sufficient to inhibit flocculation. Once the test has been standardized with one type of body fluid, for example, urine, another type of body fluid, for example, serum, may not be substituted, and a separate test must be set up for this.

Since the presence of agglutination is easily visualized by the naked eye, the present test serves as an extremely sensitive assay method for the detection of opium alkaloids, such as morphine, codeine, or heroin. Thus, once the test has been standardized as mentioned above, the presence of nanogram quantities of these opium alkaloids in body fluids can easily be detected by noting the inhibition of agglutination caused by the presence of such alkaloids in the body fluid, as compared with the agglutination resulting when opium alkaloid free body fluid is employed.

The test can be standardized so that a medically and statistically meaningful cut-off point is established. Thus, quantities of opium alkaloid in body fluid greater than this amount will cause inhibition of flocculation (a positive test for the presence of such drug in the body fluid) and quantities less than this amount will not inhibit flocculation (a negative test).

The above described reagents can be conveniently packaged for commercial purposes, e.g., in a diagnostic reagent kit containing two separate containers: one with the antiserum against opium alkaloids and the other with the amino lower alkyl ether of the phenolic hydroxyl group of an opium alkaloid bonded via a peptide linkage to latex particles containing carboxyl groups, most preferably in aqueous suspension.

The amino lower alkyl ethers of the phenolic hydroxyl group of an opium alkaloid can also be linked to immunogenic carrier materials such as proteins or polypeptides by means of an amide linkage to afford antigens which are useful for the elicitation of antibodies specific for opium alkaloids. The method of linkage to immunogenic carrier materials, as well as the elicitation of antibodies, are generally described in U.S. Pat. No. 3,709,868 for the corresponding carboxy lower alkyl ethers of opium alkaloids.

The invention is further explained and illustrated in the following examples:

EXAMPLE 1

3-(3-Phthalimidopropoxy)-7,8-didehydro-4,5 α-epoxy-17-methylmorphinan-6 α-ol

A stirred solution of 25.0 g (87.7 mmol) of morphine in 350 ml of hexamethylphosphoramide was cooled in an ice-water bath and 10.3 g (92.0 mmol) of potassium tertiary butoxide was added through a Gooch tube over a period of 10 minutes. After stirring at room temperature for 0.5 hr, 23.5 g (87.7 mmol) of N-(3-bromopropyl)-phthalimide was added and stirring was continued at this temperature for 21 hrs. The reaction mixture was poured into 500 ml of ice-water and then 500 ml of ethyl acetate was added. The organic phase was separated and the aqueous solution was extracted with 500 ml of ethyl acetate. The combined ethyl acetate extracts were washed with water (3 × 250 ml), 2 N sodium hydroxide, and with water (3 × 300 ml). After drying, the solvent was removed in vacuo to give 31.0 g of crude product, which after recrystallization from isopropanol—ether, yielded pure 3-(3-phthalimidopropoxy)-7,8-didehydro-4,5 α-epoxy- 17-methylmorphinan-6 α-ol, m.p. 121°–123°, $[\alpha]_D^{25}$ −76.63° (c 1.03, MeOH).

Anal. Calcd. for $C_{28}H_{28}N_2O_5$ (472.52): C, 71.17; H, 5.97; N, 5.93. Found: C, 70.93; H, 6.10; N, 5.86.

EXAMPLE 2

3-(3-Aminopropoxy)-7,8-didehydro-4,5α-epoxy-17-methylmorphinan-6 α-ol (3-O-Aminopropylmorphine)

To a 13.4% solution of methylamine in 100 ml of abs. ethanol was added 5.0 g (10.7 mmol) of 3-(3-phthalimidopropoxy)-7,8-didehydro-4,5α-epoxy-17-methylmorphinan-6 α-ol. After stirring at room temperature for 3.5 hrs, the reaction mixture was concentrated to a volume of about 50 ml and diluted with 200 ml of water and 200 ml of chloroform. The organic solution was separated and the aqueous phase was extracted with chloroform (2 × 200 ml). The combined chloroform solution was extracted with 1 N hydrochloric acid (2 × 100 ml). The acidic extracts were combined and made basic with 2 N sodium hydroxide (150 ml). The aqueous suspension was extracted with chloroform (3 × 200 ml). The chloroform solution was washed with water (2 × 200 ml) and dried. Removal of solvent in vacuo afforded 3.8 g of crude product, which, after recrystallization from benzene-ether, yielded pure 3-(3-aminopropoxy)-7,8-didehydro-4,5α-epoxy-17-methylmorphinan-6α-ol, m.p. 132°–134°[$\alpha]_D^{25}$ −110.2°(c 1.06, MeOH).

Anal. Calcd. for $C_{20}H_{26}N_2O_3$ (342.42): C, 70.15; H, 7.63; N, 8.18. Found: C, 70.34; H, 7.79; N, 8.19.

EXAMPLE 3

3-(3-Cyanopropoxy)-7,8-didehydro-4,5α-epoxy-17-methylmorphinan-6α-ol

To a solution of 0.973 g of sodium dissolved in 100 ml of abs. ethanol was added 12.1 g (0.042 mol) of morphine. After heating at reflux for 1 hr, the reaction mixture was cooled to room temperature and 6.3 g of 4-bromobutyronitrile was added; then heating under reflux was resumed for 16 hr. After removal of the ethanol, the residue was dissolved in chloroform (150 ml). The chloroform solution was washed with 2 N sodium hydroxide (2 × 50 ml) and with water (50 ml). After drying, the solvent was removed in vacuo to give 14.0 g of crude 3-(3-cyanopropoxy)-7,8-didehydro-4,5 α-epoxy-17-methylmorphinan-6 α-ol. A sample of this compound was distilled, b.p. 260°–265°/0.25 mm; $[\alpha]_D^{25}$ −104.09°(c 1.06, MeOH).

Anal. Calcd. for $C_{21}H_{24}N_2O_3$ (352.42): C, 71.57; H, 6.86; N, 7.95. Found: C, 71.38; H, 6.83; N, 7.85.

EXAMPLE 4

3-(4-Aminobutoxy)-7,8-didehydro-4,5 α-epoxy-17-methylmorphinan-6α-ol (3-O-aminobutylmorphine)

To a suspension of 2.0 g of lithium aluminum hydride in 100 ml of anhydrous ether was added dropwise a solution of 3.1 g (0.009 mol) of 3-(3-cyanopropoxy)-7,8-didehydro-4,5 α-epoxy-17-methylmorphinan-6 α-ol in 25 ml of dry benzene. After the mixture had been refluxed for 16 hr, it was cooled to room temperature and 10 ml of ethyl acetate followed by 10 ml of water (saturated with sodium chloride) were added dropwise. The resulting suspension was diluted with 150 ml of dioxane, dried, and filtered. The filtrate, on concentration in vacuo afforded 2.9 g of crude amine, which after recrystallization from benzene, yielded pure 3-(4-aminobutoxy-7,8-didehydro-4,5α-epoxy-17-methylmorphinan-6 α-ol, m.p. 140°–142°, $[\alpha]_D^{25}$ −104.4°(c 1.02, MeOH).

Anal. Calcd. for $C_{21}H_{28}N_2O_3$ (356.45): C, 70.76; H, 7.92; N, 7.86. Found: C, 70.72; H, 7.91; N, 7.56.

EXAMPLE 5

Preparation of Morphine Latex Polymer — General Procedure

3-O-Aminopropylmorphine is reacted with a latex suspension in the presence of 1-cyclohexyl-3-(2-morpholino-ethyl)carbodiimide metho p-toluenesulfonate. The resultant complex is washed by repeated sedimentation of the solid latex particles by centrifugation and resuspension in an appropriate buffer until no free aminopropylmorphine is left in the aqueous phase of the suspension. The aminopropylmorphine is used at a concentration of 1 mg per ml in distilled water. The solution is adjusted to pH 5.0. The latex suspension is a carboxylated styrene butadiene copolymer (Dow Chemical Corp. No. 816), which has been washed and then diluted in water to contain approximately 5% latex solids. The concentration of the carbodiimide used is 1% weight/volume in distilled water. The reaction mixture is comprised of the following ratio of reactants: 1 volume of 1% carbodiimide, one volume of aminopropylmorphine and 6 volumes of latex polymer suspension. The reaction is allowed to proceed at room temperature overnight for 16 hrs. under continuous agitation. The solid polymer complex is then sedimented by centrifugation, washed with water and resuspended in 0.1 M tris saline buffer, pH 7.3 to a final concentration of 80 mg solids/ml.

EXAMPLE 6

Preparation of Antiserum for Test

Rabbit antiserum against opium alkaloids, prepared as described in U.S. Pat. No. 3,709,868, is diluted in an appropriate buffer system. This diluent consists of the following in aqueous solution at pH 6.5:
1. 0.1% Sodium azide
2. 1% Bovine albumin, highly purified
3. 0.01% EDTA Ethylene diamine tetra acetate in the disodium form
4. MES [0.1 Molar 2-(N-Morpholino) Ethane Sulfonic Acid]

EXAMPLE 7

Test Methodology

One ml of diluted antiserum prepared as in Example 6 is dispensed into small test tubes 7 × 75 mm. To this quantity is added 200 microliters of morphine free urine. The two fluids are mixed and left to incubate at 37°C for 10 mins. Ten microliters of diluted aqueous aminopropylmorphine latex suspension containing approximately 1.25% latex solids by weight is added and mixed with the antiserum and urine. The final solution contains approximately 600 nanograms/ml of aminopropylmorphine equivalents. The test tubes are then placed into a 37°C water bath or heat block so that approximately ¼ of the liquid column in the test tube is underwater or inside the metal block. The appearance of the liquid in the tubes is translucent, turbid, or slightly milky. Starting approximately 45 mins. after the beginning of incubation fine floccules are visible in the tube. Large, easily visible floccules become evident during the second hour of incubation and tend to settle out leaving the liquid increasingly more clear and transparent.

The dilution of a particular antiserum which is chosen for the test system is the one which has the highest dilution while still producing a strong flocculation after 2 hrs, as described above. When various amounts of morphine sulfate is dissolved in morphine free normal urine and substituted for the morphine free urine in the test systems, no flocculation occurs. The amount of morphine required to inhibit the flocculation will usually vary from 100 nanograms per ml or greater depending on the concentration of antiserum used and the strength of the antiserum produced in the donor animal. It is also dependent on the amount of body fluid added. Thus, for the system described above, 200µl of urine containing 100 nanograms of morphine/ml is just sufficient to inhibit flocculation. 100µl of urine containing 200 nanograms/ml or 50µl of urine containing 400 nanograms/ml will behave the same.

We claim:
1. An immunological diagnostic reagent comprising discrete particles of latex polymer having carboxyl groups covalently bound through an amide linkage to the amino group of an amino lower alkyl ether of the phenolic hydroxyl group of an opium alkaloid.
2. The reagent of claim 1 wherein the opium alkaloid is morphine.
3. The reagent of claim 1 wherein the latex polymer is a carboxylated styrene butadiene polymer having a specific gravity about that of water and a particle size of about 0.1 to about 0.3 microns.
4. The reagent of claim 1 wherein the amino lower alkyl ether of the phenolic hydroxyl group of the opium alkaloid is from about 0.01 to about 15.0% by weight of the total reagent.
5. A method of detecting the presence of opium alkaloids in body fluid which comprises observing the inhibition of agglutination caused by said body fluid as compared with a known opium alkaloid free body fluid when said first body fluid is incubated with antiserum against opium alkaloids, and then with a reagent comprising discrete particles of latex polymer having carboxyl groups covalently bonded through an amide linkage to the amino group of an amino lower alkyl ether of the phenolic hydroxyl group of an opium alkaloid.
6. The method of claim 5 wherein the opium alkaloid detected is morphine, codeine or heroin.
7. The method of claim 5 wherein the concentration of antiserum and reagent are adjusted so that between about 10 and 40 nanograms of morphine will be just sufficient to inhibit agglutination.
8. The method of claim 5 wherein the body fluid is urine.

* * * * *